US00PP33836P2

(12) United States Plant Patent
Hampson et al.

(10) Patent No.: US PP33,836 P2
(45) Date of Patent: Jan. 11, 2022

(54) ***MALUS* TREE NAMED '8S5505'**

(50) Latin Name: *Malus domestica*
Varietal Denomination: 8S5505

(71) Applicant: Her Majesty the Queen in Right of Canada as Represented by the Minister of Agriculture and Agri-Food, Ottawa (CA)

(72) Inventors: Cheryl Hampson, Summerland (CA); Richard MacDonald, Summerland (CA)

(73) Assignee: HER MAJESTY THE QUEEN IN RIGHT OF CANADA AS REPRESENTED BY THE MINISTER OF AGRICULTURE AND AGRI-FOOD, Ottawa (CA)

( * ) Notice: Subject to any disclaimer, the term of this patent is extended or adjusted under 35 U.S.C. 154(b) by 0 days.

(21) Appl. No.: 17/106,342

(22) Filed: Nov. 30, 2020

Related U.S. Application Data

(60) Provisional application No. 62/974,365, filed on Dec. 2, 2019.

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
CPC ..... A01H 6/7418
See application file for complete search history.

*Primary Examiner* — Anne Marie Grunberg
(74) *Attorney, Agent, or Firm* — Penny J. Aguirre

(57) ABSTRACT

A new cultivar of apple tree named '8S5505' that is characterized by its fruit that is flavorful with aromatic tropical notes, its fruit that is crisp, its fruit that is juicy, its fruit with excellent storage life, fruit with excellent shelf life, its trees with strong lateral growth, its high disease resistance to 'apple scab' (*Venturia inaequalis*) due to the presence of the VF gene and its mid-season bloom period (similar timing to Golden Delicious).

3 Drawing Sheets

Botanical classification: *Malus domestica.*
Varietal denomination: '8S5505'.

BACKGROUND OF THE INVENTION

The present invention relates to a new and distinct cultivar of apple tree, botanically known as *Malus domestica* '8S5505', referred to hereafter by its cultivar name, '8S5505'. '8S5505' is a new cultivar of apple tree grown for the fresh food market.

The new cultivar arose from a *Malus domestica* cross made by the Inventor in Summerland, British Columbia, Canada in 2000 between a proprietary plant in the Inventor's breeding program named '8S6923' (not patented) as the female parent and 'Co-op 25' (U.S. Plant Pat. No. 12,323) as the male parent. The Inventor selected '8S5505' in 2006 as a single unique plant amongst the seedlings that resulted from the above cross.

Asexual propagation of the new cultivar was first accomplished by vegetative budding in 2007 under the direction of the Inventor in Summerland, BC, Canada. Asexual propagation by vegetative budding and grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish '8S5505' as a unique cultivar of apple tree.

1. '8S5505' exhibits fruit that is flavorful with aromatic tropical notes.
2. '8S5505' exhibits fruit that is crisp.
3. '8S5505' exhibits fruit that is juicy.
4. '8S5505' exhibits fruit with excellent storage life.
5. '8S5505' exhibits fruit with excellent shelf life.
6. '8S5505' exhibits trees with strong lateral growth.
7. '8S5505' exhibits high disease resistance to 'apple scab' (*Venturia inaequalis*) due to the presence of the VF gene.
8. '8S5505' exhibits mid-season bloom period (similar timing to Golden Delicious).

The female parent of '8S5505, differs from '8S5505' in having fruit that is all yellow in color, fruit that is less firm, has a longer stem, and develops less burr knots on the tree trunk. The male parent of '8S5505', is similar to '8S5505' in having trees that are very productive and highly scab resistant due to the VF gene. The male parent of '8S5505' differs from '8S5505' in having fruit that is darker red in color with more overcoloring, a later blooming time, and in not produce fruit annually if over-cropped. '8S5505' can also be compared to the cultivar 'Ambrosia' (U.S. Plant Pat. No. 10,789). 'Ambrosia' is similar to '8S5505' in having fruit that is red and yellow in color. 'Ambrosia' differs from '8S5505' in being susceptible to apple scab (*Venturia inaequalis*), in developing less branches and in having fruit that is conic shaped, less dense, and breaks down more rapidly in air storage at 1° C. with no treatments.

BRIEF DESCRIPTION OF THE DRAWINGS

The accompanying colored photographs illustrate the overall appearance and distinct characteristics of the new

*Malus*. The photographs were taken of a ten-year-old tree of '8S5505' as grown outdoors in the ground in Summerland, BC, Canada.

Figure 1:
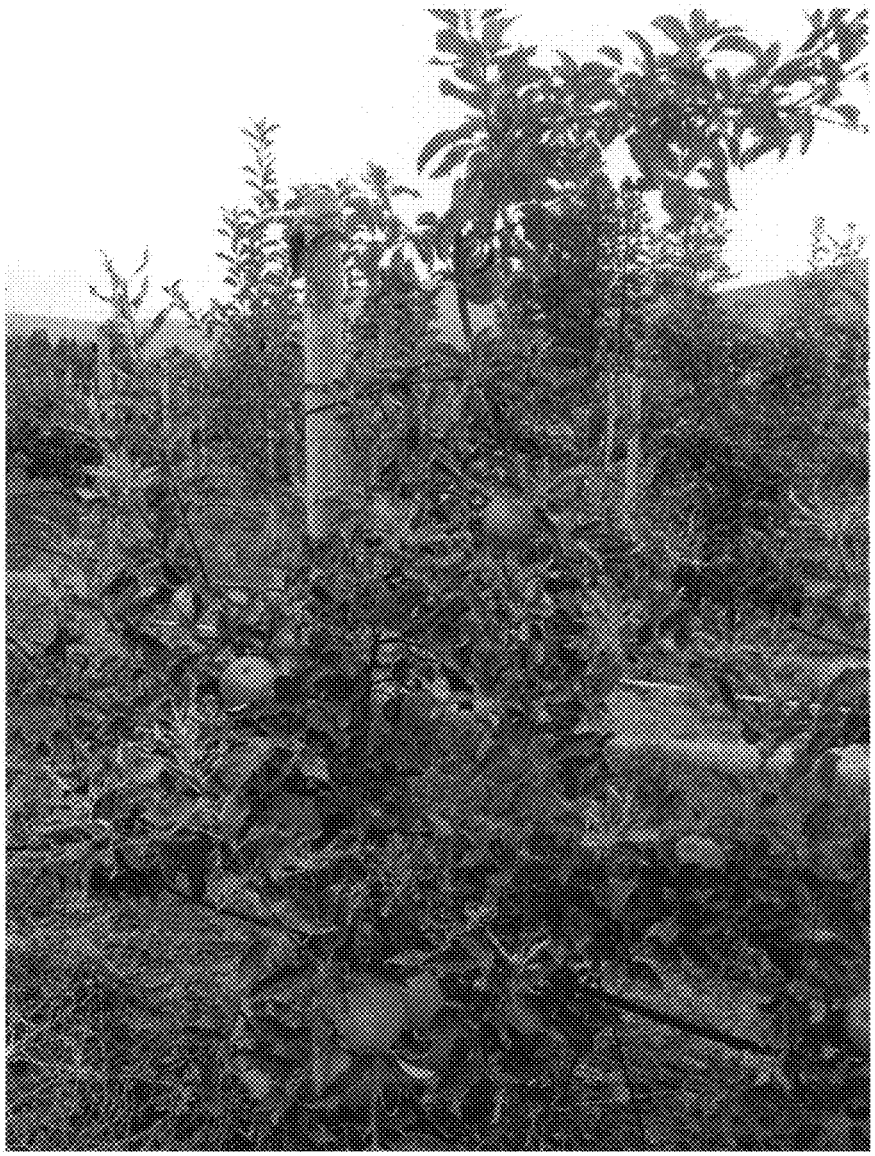

The photograph in FIG. 1 provides a side view of '8S5505' in the ground.

Figure 2:
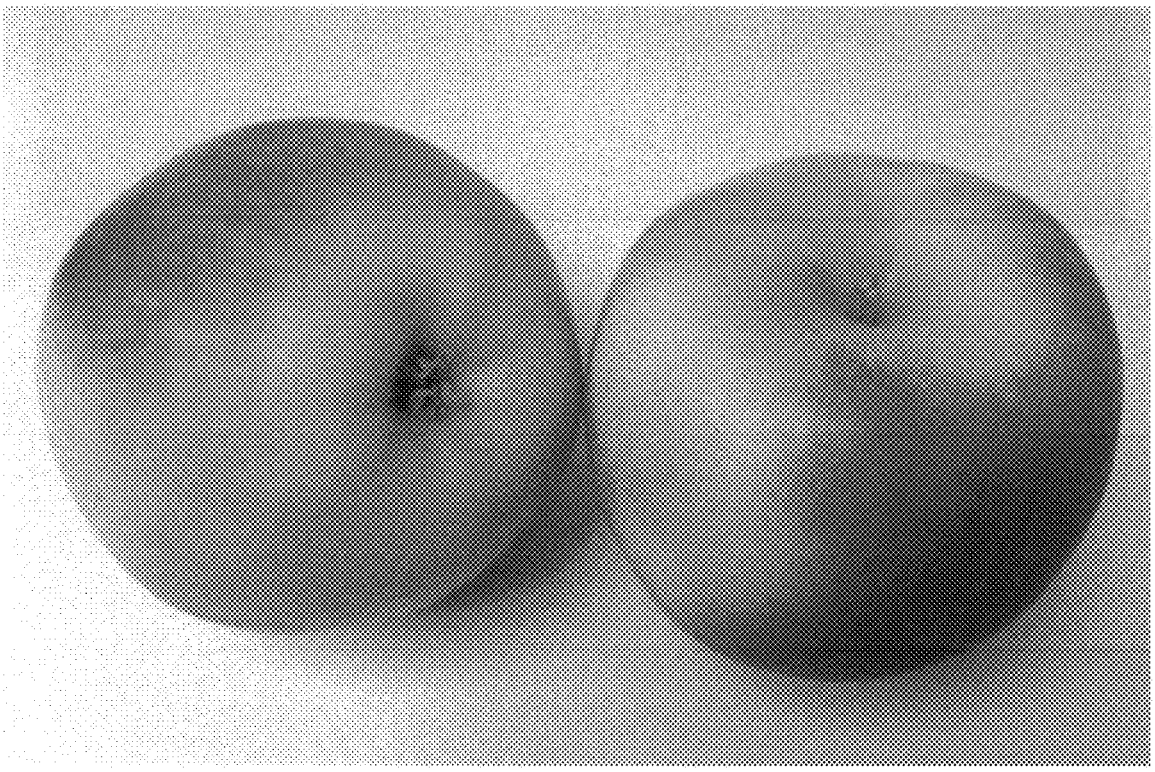

The photograph in FIG. 2 provides a close-up-view of the fruit of '8S5505'.

Figure 3:
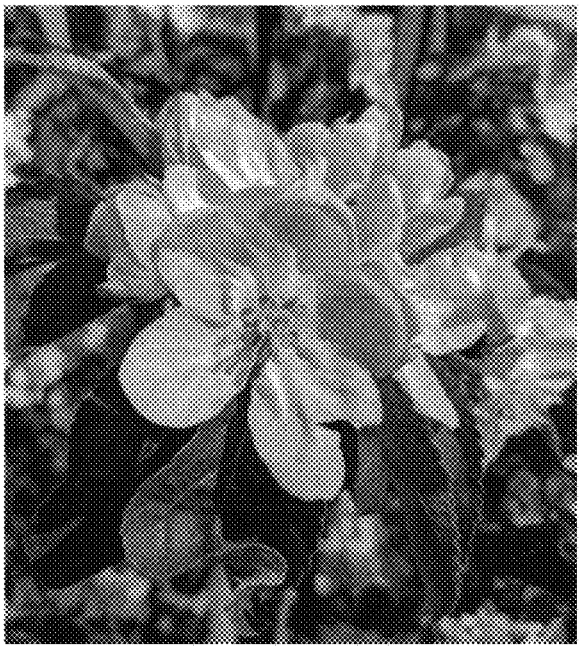

The photograph is FIG. 3 provides a close-up view of the flowers of '8S5505'.

Figure 4:
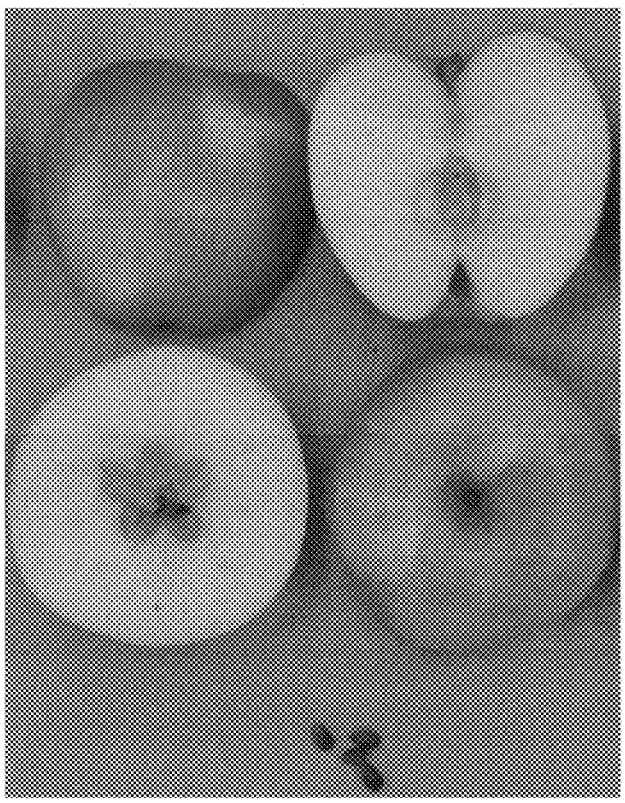

The photograph in FIG. 4 provides a view of the cut fruit of '8S5505'.

The colors in the photographs are as close as possible with the photographic and printing technology utilized and the color values cited in the detailed botanical description accurately describe the colors of the new apple tree.

DETAILED BOTANICAL DESCRIPTION

The following is a detailed description of ten-year-old plants of '8S5505' as grown outdoors in the ground in Summerland, BC, Canada. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

Tree description:

*Plant type.*—Deciduous fruiting tree.

*Plant habit.*—Spreading.

*Height and spread.*—An average of 2.01 m in height and 1.83 m in width as a ten-year-old plant in an orchard.

*Cold hardiness.*—At least to U.S.D.A. Zone 4.

*Diseases and pests.*—Has shown high resistance to 'apple scab' (*Venturia inaequalis*) due to the presence of the VF gene, no susceptibility or resistance to pests has been observed.

*Propagation.*—Vegetative budding and grafting, grown on rootstock.

*Roots.*—Fibrous, 200B in color.

*Root development.*—1 year (time to produce a young plant from budding).

*Growth rate.*—Strong lateral growth, moderate vertical.

*Trunk.*—Burr knots develop with tree age.

Description of branches:

*Branching habit.*—Medium to high.

*Branch angle.*—Average of 90° to the trunk.

*Branch bearing.*—Predominance of bearing on spurs.

*Bark color.*—197D overcolor, 165B undercolor.

Description of one-year-old shoots:

*Branch surface.*—Moderately glossy, medium to densely covered with pubescence, moderately covered with lenticels; oval in shape, <1 mm in length and diameter, 7 per square cm of shoot, 162D in color.

*Branch strength.*—Medium strength with moderate flexibility.

*Internode length.*—Average of 2.8 cm.

*Branch color.*—175A.

*Branch angle.*—Held in an average angle of 45°.

*Growth pattern.*—Straight.

Description of growing shoots:

*Color of growing tip of shoot.*—Without pubescence 145B.

*Shape of shoot tips leaves in cross section.*—Narrow elliptic with acute tip and base.

*Pubescence of shoot tip leaves.*—Present, moderate to heavy.

*Color of shoot tip leaves.*—145B.

*Distribution of color other than green on shoot tips leaves.*—Without pubescence, 145B.

*Vegetative buds.*—Adpressed in relation to shoots, acute in shape, bud support small in size; an average of 1.5 mm in length and 1 mm in width.

Leaf description:

*Leaf orientation.*—Outwards.

*Leaf division.*—Simple.

*Leaf shape.*—Ovate with an acute tip.

*Leaf size.*—Average of 8 cm in length and 5.4 cm in width.

*Leaf tip.*—An average of 9.82 cm in length.

*Leaf apex.*—Acute.

*Leaf base.*—Rounded.

*Leaf surface.*—Upper surface; glabrous.

*Leaf margin.*—Serrate with occasional biserrate, incisions are an average of 1.66 mm in depth, very weak undulation.

*Leaf blade profile in cross-section.*—Slightly obtuse-V-shaped.

*Leaf color.*—Upper surface 137A, lower surface 138B.

*Leaf anthocyanin on lower surface.*—None.

*Leaf venation.*—Main veins pinnate, minor veins netted, 145B in color.

*Petiole size.*—Average of 1.78 cm in length and 2 mm in diameter.

*Petiole color.*—A blend of 137A and 145B, 187A at the base.

*Stipules.*—Average of 2, 137A in color, average of 1.39 cm in length and 2.3 mm in width, found on actively growing shoots and newly developed leaves but sometimes abscising on older leaves.

Flower description:

*Blooming period.*—Mid-season; early May in Summerland, British Columbia, Canada.

*Number of flowers.*—Average of 5 per spur; very precocious.

*Inflorescence type.*—Corymb of rotate flowers.

*Flower buds.*—Elliptic to round in shape, 60A in color.

*Flower size.*—Average of 4.8 cm in diameter, 1.36 cm in height, and 2.2 cm in depth.

*Flower fragrance.*—Mild.

*Flower aspect.*—Upright.

*Flower shape.*—Shallow cupped.

*Petals.*—5 per flower, unfused, sometimes overlapping, circular in shape, rounded apex, round base, entire, smooth margins, about 2.1 cm in length, 1.5 cm in width, color of upper and lower surfaces when opening and mature; 155D, tinged with186B, both surfaces glabrous.

*Sepals.*—5, very narrowly triangular in shape, entire, smooth margins, very acute apex, fused base, average of 1 cm in length and 3.7 mm in width, color of upper and lower surface; 144B, upper surface moderately pubescence, lower surface densely pubescent.

*Pedicel.*—Average of 2.4 cm in length, 143A in color, 1.7 mm in width, surfaces is moderately covered with pubescence.

*Pistil.*—19, compound carpel with 5 stigmas fused at base (circular in shape), 1.24 cm in length, style; 145B in color, 8.2 mm in length, stigma; 145B in color and held above the anthers, ovary; moderately pubescent, 143A in color.

*Stamens.*—Average of 15 stamens, 155D in color, 7.8 mm in length, anther; oblong in shape, pollen; 5C in color and moderate in quantity.

*Pollination requirement.*—Cross pollination required.

Fruit description:

*Fruit size.*—Medium, 8.5 cm in diameter, average of 7.1 cm in height.

*Position of maximum diameter.*—Midway between proximal and distal ends.

*Fruit shape.*—Conic to globose conical.

*Fruit symmetry.*—Symmetrical.

*Fruit prominence of ribbing.*—Moderately present.

*Fruit aperture of eye.*—Closed to semi-open, an average of 8.7 mm in diameter.

*Persistence of calyx.*—Persistent.

*Length of sepal.*—Average of 8.2 mm.

*Spacing of sepals at base.*—Touching to overlapping.

*Eye basin.*—Narrow and shallow, an average of 8.5 mm in depth and 2.91 cm in width.

*Stalk.*—An average of 2.8 mm in thickness, 1.89 cm in length.

*Depth of stalk cavity.*—Medium to wide stalk cavity width, medium depth, an average of 2.06 cm in depth and 4.09 cm in width.

*Relief of surface.*—Smooth.

*Skin.*—Medium waxiness, bloom not present, translucent, thin, and smooth.

*Skin color.*—Overcolor 45A and 23A and ground color 13C, overcolor on young fruit is small to medium, percent of overcolor on mature fruit is an average of 52%, pattern of overcolor is flushed and mottled with occasional faint, wide striping around the crown (average of 3.5 mm in width).

*Presence of russet.*—Generally not present.

*Lenticels.*—Small to medium (average of <1 mm), moderately prominent.

*Color of flesh.*—4D.

*Distinctness of core line.*—Low to medium.

*Aperture of locules.*—Open.

*Fruit set.*—Good.

*Fruit maturity date.*—Mid-late season; average harvest date is September 29th in Summerland, BC, Canada.

*Browning of flesh.*—Medium.

*Firmness* (*without skin*).—Firm to very firm (average of 21.6 lbs).

*Texture of flesh.*—Crisp.

*Cropping frequency.*—Annual.

*Fruit yield.*—An average of 15.9 kg/tree (slender spindle).

*Acidity.*—An average of 0.6 g/L titratable acidity (malic acid equivalent).

*Brix.*—An average of 13.8%.

*Seed.*—Ranges from 166A to 165B when dry, elongated ovate with an acute tip, an average of 1 cm in length and 4.7 mm in width and 2.4 mm in thickness.

*Storage life.*—Minimum of 6 months in air storage (average temperature of 1° C.).

*Market use.*—Fresh fruit.

It is claimed:

1. A new and distinct variety of apple tree named '8S5505' as herein illustrated and described.

* * * * *